(12) United States Patent
Lipman et al.

(10) Patent No.: US 8,992,625 B2
(45) Date of Patent: Mar. 31, 2015

(54) POSTERIOR STABILIZED KNEE PROSTHESIS

(75) Inventors: Joseph David Lipman, New York, NY (US); Anna Rabinowitz, New York, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 0 days.

(21) Appl. No.: 12/970,424

(22) Filed: Dec. 16, 2010

(65) Prior Publication Data

US 2011/0118847 A1  May 19, 2011

Related U.S. Application Data

(62) Division of application No. 11/860,423, filed on Sep. 24, 2007, now Pat. No. 7,875,081.

(60) Provisional application No. 60/826,844, filed on Sep. 25, 2006.

(51) Int. Cl.
*A61F 2/38* (2006.01)
*A61F 2/30* (2006.01)

(52) U.S. Cl.
CPC ............. *A61F 2/3886* (2013.01); *A61F 2/3859* (2013.01); *A61F 2/389* (2013.01); *A61F 2002/30301* (2013.01); *A61F 2230/0095* (2013.01)
USPC ..................................................... 623/20.27

(58) Field of Classification Search
CPC ................................. A61F 2/38; A61F 2/3859
USPC ........................................................ 623/20.27
See application file for complete search history.

(56) References Cited

U.S. PATENT DOCUMENTS

| 3,840,905 | A | 10/1974 | Deane |
| 4,064,568 | A | 12/1977 | Grundei et al. |
| 4,209,861 | A | 7/1980 | Walker et al. |
| 4,213,209 | A | 7/1980 | Insall et al. |
| 4,298,992 | A | 11/1981 | Burstein et al. |
| 4,888,021 | A | 12/1989 | Forte et al. |

(Continued)

FOREIGN PATENT DOCUMENTS

| FR | 2709662 | 3/1995 |
| FR | 2844704 | 3/2004 |

(Continued)

OTHER PUBLICATIONS

Hanson, George et al., In Vivo Anterior Tibial Post Contact after Posterior Stabilizing Total Knee ArthroDiastv, Journal of Orthopaedic Research, Mar. 2007.

(Continued)

*Primary Examiner* — Bruce E Snow
*Assistant Examiner* — Melissa Hoban
(74) *Attorney, Agent, or Firm* — Leason Ellis LLP

(57) ABSTRACT

A femoral component for a knee joint prosthesis is formed of a body having an anterior side, a posterior side, and pair of laterally spaced condylar portions. The femoral component includes an intercondylar portion that joins the condylar portions and includes a recess. The intercondylar portion has an arcuate shaped roof that extends between a pair of opposing side walls. The arcuate shaped roof is formed so as to be defined by a single radius.

13 Claims, 5 Drawing Sheets

(56) References Cited

U.S. PATENT DOCUMENTS

| | | | |
|---|---|---|---|
| 5,358,527 | A | 10/1994 | Forte |
| 5,554,158 | A * | 9/1996 | Vinciguerra et al. ........... 606/80 |
| 5,639,279 | A | 6/1997 | Burkinshaw et al. |
| 5,702,458 | A | 12/1997 | Burstein et al. |
| 6,039,764 | A | 3/2000 | Pottenger et al. |
| 6,443,991 | B1 | 9/2002 | Running |
| 7,081,137 | B1 | 7/2006 | Servidio |
| 2003/0004577 | A1 | 1/2003 | Running |
| 2004/0143338 | A1 | 7/2004 | Burkinshaw et al. |

FOREIGN PATENT DOCUMENTS

| | | |
|---|---|---|
| JP | 54-156394 | 12/1979 |
| JP | 10-513371 | 12/1998 |
| JP | 2001-524349 | 12/2001 |
| JP | 2006-15133 | 1/2006 |
| JP | 2006-511278 | 4/2006 |
| WO | WO-2005/072657 | 8/2005 |

OTHER PUBLICATIONS

Li, Guoan et al., Anterior tibial post impingement in a posterior stabilized total knee arthroplasty, Journal of Orthopaedic Research, vol. 23 (2005) pp. 536-541.

Puloski, S.K.T., et al. Tibial Post Wear in Posterior—Stabilized Total Knee Arthroplasty: An Unrecognized Source of Polyethylene Debris, The Journal of Bone &Joint Surgery, vol. 83-A,D, No. 3, DO. 390-397, Mar. 2001.

Huang, Chang-Hung, et al., Stress Analysis of the Anterior Tibial Post in Posterior Stabilized Knee Prostheses, Journal of Orthopaedic Research, Apr. 2007.

Callaghan, John J. et al., Tibial Post Impingement in Posterior-Stabilized Total Knee, Arthroplasty, Clinical Orthopaedics and Related Research, No. 404 pp. 83-88 (2002).

* cited by examiner

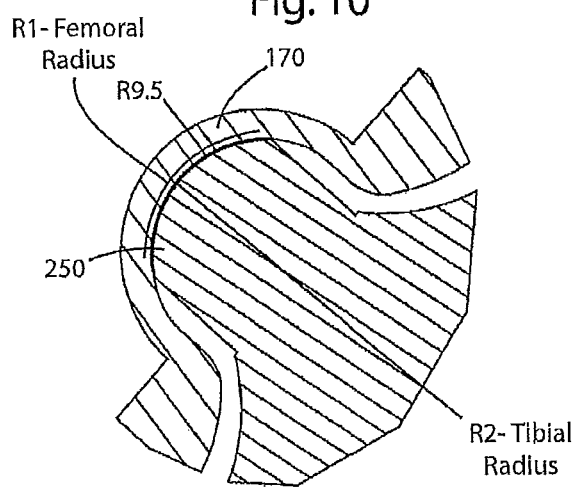
Fig. 10
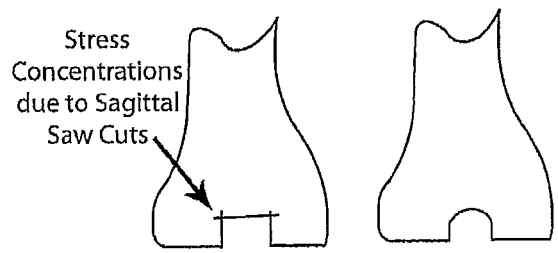
Fig. 11
Fig. 12
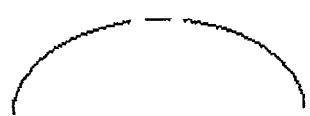

POSTERIOR STABILIZED KNEE PROSTHESIS

CROSS-REFERENCE TO RELATED APPLICATION

The present application is a divisional application of U.S. patent application Ser. No. 11/860,423 filed Sep. 24, 2007 which claims the benefit of U.S. provisional patent application No. 60/826,844, filed Sep. 25, 2006, which are hereby incorporated by reference in their entirety.

TECHNICAL FIELD

The present invention relates generally to joint replacement surgery and more particularly, to a posterior stabilized knee prosthesis that includes a modified femoral anterior cam surface and a modified anterior face of a stabilizing post of a tibial insert that results in a reduction of stresses at these surfaces and a reduction in deformation of the anterior face of the post, as well as a reduction in the amount of bone that is removed during the surgery.

BACKGROUND

Joint replacement surgery is quite common and it enables many individuals to function normally when they otherwise would not be possible to do so. Typically, an artificial joint includes metallic, ceramic and/or plastic components that are fixed to existing bone. One of the more common joints that undergoes replacement surgery is the knee. Knee arthroplasty is a well known surgical procedure by which a diseased and/or damaged natural knee joint is replaced with a prosthetic knee joint. A typical knee prosthesis includes a femoral component, a patella component, a tibial tray or plateau and a tibial bearing insert coupled to the tibial tray. The femoral component generally includes a pair of laterally spaced apart condylar portions that have distal surfaces that articulate with complementary condylar elements formed in a tibial bearing insert.

Total knee prostheses can essentially be classified into three basic categories based on the techniques and components involved in the surgery. In a first category, the articular surface of the distal femur and proximal tibia are "resurfaced" with respective condylar-type articular bearing components. These knee prostheses provide substantial rotational and translational freedom and require minimal bone resection to accommodate the components in the available joint space. The patella-femoral joint may also be resurfaced by a third prosthetic component, as well. The femoral, tibial and patella prosthetic resurfacing components are affixed to respective adjacent bone structure by a cementing or by a biological bone ingrowth fixation means or any other suitable technique.

The femoral component provides medial and lateral condylar bearing surfaces of multi-radius design of similar shape and geometry as the natural distal femur or femoral-side of the knee joint. The tibial component can be made entirely of plastic (UHMWPE: ultra-high molecular weight polyethylene) or it can be made of a metallic base component and interlocking plastic component. The plastic tibial bearing surface can be of concave multi-radius geometry to more or less match the mating femoral condyles. Both the femoral and tibial components are independently positioned on either side of the knee joint and are not mechanically connected or linked together, as in the case of hinged type of knee prostheses, which constitutes the secondary category of total knee prostheses.

In resurfacing types of total knee prostheses according to the first category, the tibial bearing surface geometry can assume a variety of configurations, depending upon the desired extent of articular contact congruency and associated translational (medial-lateral and anterior-posterior) and rotational (axial and varus-valgus) secondary femoro-tibial motions. These various secondary motions allow the resurfaced knee to function in a natural-like biomechanical manner in conjunction with the surrounding ligamentous and muscle structures about the knee joint. The soft tissue structures maintain the femoral and tibial bearing surfaces in contact, provide the necessary levels of force constraint to achieve knee joint stability, and functionally decelerate the principal motion in flexion-extension and secondary motions, such as axial rotation, in a controlled manner. Additionally, this functional interaction between the surrounding tissue structures and the implanted knee prosthesis minimizes abrupt motion stoppage or impact loading of the prosthetic articular surfaces, thus preventing overstressing at the component fixation interface.

According to the second category, a mechanically linked, or hinged type of knee prosthesis provides a fixed fulcrum flexion-extension capability. The "hinged knee" therefore is usually surgically indicated in selected cases where the surrounding soft tissue structures are grossly degenerated and incapable of providing functionally acceptable knee joint stability.

The third category of total knee prosthetic devices, the posterior stabilized total knee provides more predictable kinematics than the first category. The posterior-stabilized total knee devices essentially incorporate all of the functional features of the first category, that is, the resurfacing condylar-type of knee prostheses, in addition to incorporating a mechanical cam/follower mechanism for providing posterior (tibia-to-femur) constraint. The cam/follower mechanism is positioned within the intercondylar space of the femoral component and provides substitutional posterior constraint, as a predesigned compensation feature for lost posterior cruciate function or for compromised posterior knee stability. This cam/follower mechanism enables the femur to 'roll-back' on the tibia providing a mechanical advantage to the quadriceps during flexion.

The cam portion of the cam/follower mechanism, generally includes a convex lobe shaped surface, integrally machined or cast within a box-like structure known as the "stabilizer box," located between the medial and lateral condyle bearing surfaces of the femoral component as shown in FIG. 1. The stabilizer box can also be referred to as being an intercondylar portion of the femoral component. The cam surface is generally formed within the posterior wall portion of the stabilizer box and is bounded by the superior wall on the top, the medial and lateral wall portions on the sides and the anterior portion. The stabilizer box structure, thus formed, occupies a significant envelope, relative to the overall dimensions of the femoral component and therefore, requires a substantial resection of viable bone to allow its accommodation within the intercondylar sector of the distal femur.

The posteriorly positioned articular convex surface of the cam is precisely ground and highly polished. The convex cam articulates with the anteriorly positioned and posteriorly oriented follower, as the knee undergoes femoro-tibial flexion. The mating follower surface is typically machined integral within the ultra-high molecular weight polyethylene (UHMWPE) tibial component. The follower member usually consists of a relatively convex or flat articular surface located on the posterior side of an upwardly extending post-like structure, which is positioned between the concave medial and lateral tibial plateau bearing surfaces. The resultant action of the contacting cam/follower mechanism provides posterior stabilization or constraint of the tibial component, relative to the femoral component: generally from about mid-range to full range of flexion. Within this limited range, therefore, the stabilizing mechanism essentially simulates the functional contribution of the natural posterior cruciate ligaments attached between the anterior femur and posterior tibia aspects of the knee joint. Additionally, since the cam/follower surface geometry is generally non-congruent, the mechanism can be designed to produce posterior roll-back of the femorotibial articular contact, simulating the natural biomechanical displacement characteristics of the natural knee.

Examples of posterior-stabilized total knee prostheses of the type described above, are disclosed in U.S. Pat. No. 4,209,861 to Walker; U.S. Pat. No. 4,298,992 to Burstein et al.; U.S. Pat. No. 4,213,209 to Insall et al.; and U.S. Pat. No. 4,888,021 to Forte et al. Each of the devices described in the above patents incorporates a UHMWPE tibial component with a pair of medial and lateral concave plateau bearing surfaces and a metal alloy femoral component with mating multi-radius condylar runners which ride on the bearing surfaces. The articulation of the femoral condyles with the tibial plateau bearing surfaces allows primary femoro-tibial flexion and extension, and secondary (freedom) motions of axial and varus-valgus rotations and anterior-posterior and medial-lateral translations. The knee joint reaction forces during primary or secondary motion are principally supported by the tibial bearing surfaces, and to some extent by the cam/follower surfaces, and are transferred to the underlying fixation interfaces and adjacent supportive bone structures.

Additionally, the UHMWPE tibial component incorporates an upwardly extending post-like structure which is positioned between the plateau bearing surfaces, slightly anterior of the component mid-line. The generally convex or flat follower surface is integrally machined on the posterior-side of the post. With the femoral and tibial knee components in a normally reduced, surgically implanted position, the upwardly extending tibial post extends into the stabilizer box structure located within the intercondylar space of the femoral component. Posterior tibial constraint is achieved when the posteriorly oriented face of the follower contacts the generally anteriorly oriented lobe surface of the cam.

However, there are a number of disadvantages with the geometries of conventional posterior cruciate substituting knee designs. In particular, one common complaint among knee surgeons is that posterior cruciate substituting knee replacements remove too much bone. Excessive bone removal can lead to intraoperative intercondylar fractures due to the stress concentration created by cutting out bone to accommodate the box of the design. Bone removal is also not desired in that in the event of revision surgery, the more bone available, the easier the revision surgery will be. It is therefore desirable and there is a need for an improved posterior cruciate substituting knee design that minimizes the amount of bone that is needed to be removed.

Another limitation with conventional posterior cruciate substituting knee designs is that the retrieved knee replacements show consistent deformation patterns in particular locations on the central post of the tibial insert that is typically made from UHMWPE. A common location for the damage to the tibial insert is the anterior face of the post. This deformation is often in the form of a "bowtie" pattern and is the result of the continued interaction of the implant components over time and likely occurs when the patient hyperextends their knee. In rare cases, this deformation can contribute to gross mechanical failure of the post. In view of the foregoing, there is a need for an improved posterior cruciate substituting knee design that reduces the stresses that contribute to this pattern of deformation.

SUMMARY

According to one aspect of the present invention, a tibial component for a knee joint prosthesis includes a platform having an upper surface that includes first and second laterally spaced concavities. Each concavity is adapted for receiving one condylar portion of a femoral component. The upper surface also includes a tibial post that fits within the intercondylar space of the femoral component. The tibial post has an anterior cam surface that has a saddle shaped surface ("saddle surface") which is a smooth surface that derives is name from the peculiar shape of historical horse saddles, which curve both up and down as described in more detail. The cam surface includes a saddle shaped portion that is located at an inferior part of the anterior cam surface and a transition portion that is located at a superior part of the anterior cam surface. The functional part of the anterior post is defined by the saddle shaped portion, while the convex transition portion is provided and shaped to blend the anterior portion of the cam to the top of the post.

In another aspect, a knee joint prosthesis includes a femoral component having an anterior side and a posterior side and including a pair of laterally spaced condylar portions and an intercondylar portion joining the condylar portions and including a recess. The prosthesis further includes a cam surface located adjacent the intercondylar recess on the anterior side of the femoral component, with the cam surface being defined by an at least substantially concave first radius of curvature and an at least substantially convex third radius of curvature perpendicular to the first radius of curvature so as to create a saddle type shape.

The tibial post has an anterior cam surface that is defined by an at least substantially convex second radius of curvature and an at least substantially concave fourth radius perpendicular to the second radius of curvature so as to define a saddle shaped anterior cam surface that is complementary to the saddle shaped anterior cam surface of the femoral component. The second radius of curvature is less than the first radius of curvature. According to one embodiment, the second radius of curvature is equal to or less than 95% of the first radius of curvature. The third radius of curvature is approximately 42% or less of the fourth radius of curvature.

In another aspect, the intercondylar portion of the femoral component includes a roof and has a box angle of greater than 20 degrees (e.g., 28 degrees) as measured from the roof to a plane parallel to a base (ground) plane.

By modifying the anterior cam surface of the femoral component and by modifying the anterior face of the stabilizing post of the tibial insert, a reduction of stresses (von Mises stresses in the tibial post) at these surfaces and reduced deformation of the anterior face of the tibial post are realized.

Further aspects and features of the exemplary joint prosthesis disclosed herein can be appreciated from the appended Figures and accompanying written description.

BRIEF DESCRIPTION OF THE DRAWING FIGURES

FIG. 10 is a cross-sectional view taken along the line 10-10 of FIG. 9;

FIG. 11 is a side elevation view showing the femoral bone cuts to receive the conventional femoral component and the femoral component of the present invention; and FIG. 12 is cross-sectional view of an exemplary anterior cam surface of either the tibial post or femoral component illustrating a flat formed along the arcuate surface thereof.

DETAILED DESCRIPTION OF PREFERRED EMBODIMENTS

Figure 1:
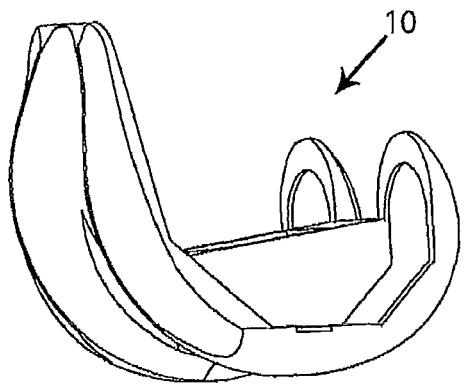
FIG. 1 is side perspective view of a conventional femoral component that forms a part of a knee joint prosthesis.

FIGS. 2-10 illustrate a joint prosthesis, in the form of a knee joint prosthesis 100 (FIG. 9), according to one exemplary embodiment of the present invention. The illustrated prosthesis 100 is of a posterior cruciate substituting knee design. The knee relies on four main ligaments to provide stability and support. There are two ligaments that cross in the center of the knee, and they are called the cruciate ligaments. The anterior cruciate ligament (ACL) prevents the femur from coming off the back of the tibia. The posterior cruciate ligament (PCL) prevents the femur from coming off the front of the tibia. Posterior stabilized knee implants are designed to be a substitute for the posterior cruciate ligament. As described in detail below, a posterior stabilized knee includes a feature, such as a post, that substitutes for the body's posterior cruciate ligament.

The prosthesis 100 generally includes a femoral component 110 (FIG. 2) for attachment to the femur and a tibial component 200 (FIG. 8) for attachment to the tibia. The femoral component 110 is formed of a body 112 that has a pair of laterally spaced-apart femoral condylar portions 114, 116, each of which is smoothly convexly curved in a lateral profile generally to approximate the curvature of an anatomical femoral condyle and is convexly curved along its anteroposterior extent. The anterior parts of the condylar portions merge smoothly with convexly curved lateral portions 122 of a patellar portion 120. A midportion 126 of the patellar portion 120 intersects at its inferior extremity a superior wall or roof 132 of a box-like intercondylar portion 130 (stabilizer box), which together with the patellar portion 120, connects the condylar portions 114, 116.

Figure 6:
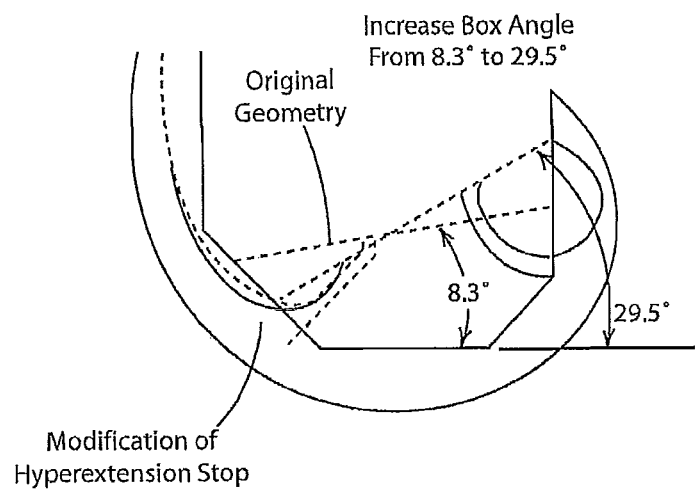
FIG. 6 is a side elevation view showing an increase in box angle in the femoral component of FIG. 2 compared to the component of FIG. 1.
Figure 7:
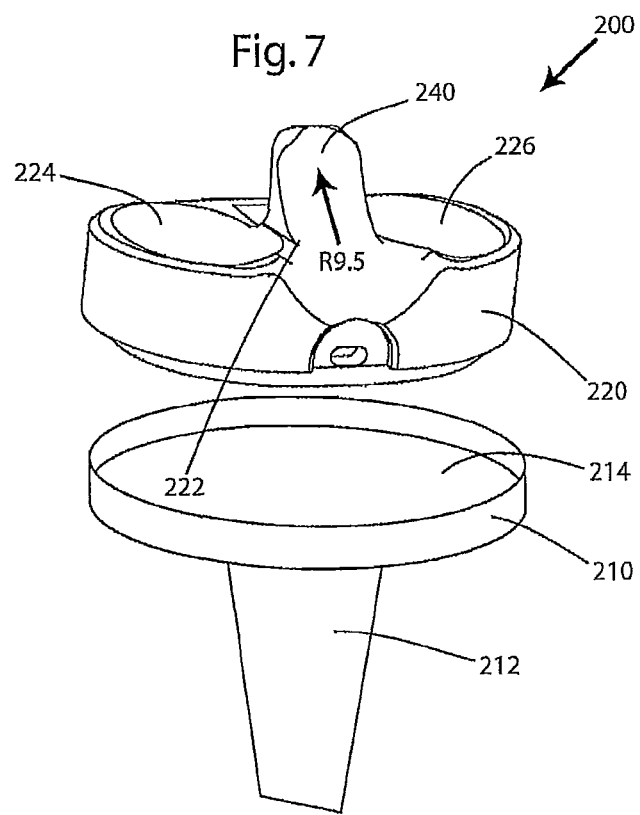
FIG. 7 is a side perspective view of a tibial component according to one embodiment of the present invention.

As shown in FIG. 1, the intercondylar portion of the conventional femoral component 10 is a rectangular-shaped box defined by a pair of laterally spaced-apart side walls that are joined by a flat perpendicular roof as shown in the side view of FIG. 1. A box angle of the intercondylar portion is about 8.3° as measured from the roof of the intercondylar portion 130 to a horizontal plane (parallel to nominal base plane) as shown in FIG. 6.

In contrast to the rectangular box shape of the intercondylar portion of the prior art femoral component 10, the design of the intercondylar portion 130 of the present invention has been modified so that the amount of bone that has to be removed is reduced. As previously mentioned, one disadvantage of the prior art implant designs is that posterior cruciate substituting knee replacement techniques remove too much bone and this excessive bone removal can lead to intraoperative intercondylar fractures due to the stress concentration created by cutting out bone to receive the box shaped intercondylar portion 130. FIG. 11 shows a section of the femur bone that has the bone removed to fit the intercondylar portion of the conventional femoral component 10 shown in FIG. 1. As would be expected, in order to accommodate the rectangular-shaped box of the conventional femoral component, a rectangular shaped bone segment is removed from the femur so as to leave a rectangular shaped notch or opening in the femur. In contrast, FIG. 11 shows an arcuate shaped bone segment removed from the femur so as to leave an arcuate shaped notch or opening in the femur to accommodate the device 100 of the present invention.

According to one exemplary embodiment, the modification in the box geometry according to the present invention results in an average reduction of about 37% in the volume of the bone removed from the intercondylar portion of the femur. This reduction in bone removal is accomplished by two means. First, the angle of the intercondylar portion 130 of the femoral component 110 is increased to minimize the bone removed anteriorly as shown in FIG. 6. For example, the box angle, as measured from a top of the roof 132, is significantly increased relative to the box angle of the conventional intercondylar portion and in the embodiment illustrated in FIGS. 2-6, the box angle is increased from 8.3° (conventional design) to about 28°. However, it will be appreciated that the above values are not limiting but are merely exemplary in nature and therefore, the box angle can be about 20 degrees to about 35 degrees, e.g., 29 degrees to about 34 degrees. In other embodiments, the box angle is increased to a value that is at least twice the value of a similar rectangular-shaped intercondylar box construction. The increased height of the posterior box does not remove much bone as there is minimal bone in this region of the femur.

Figure 2:
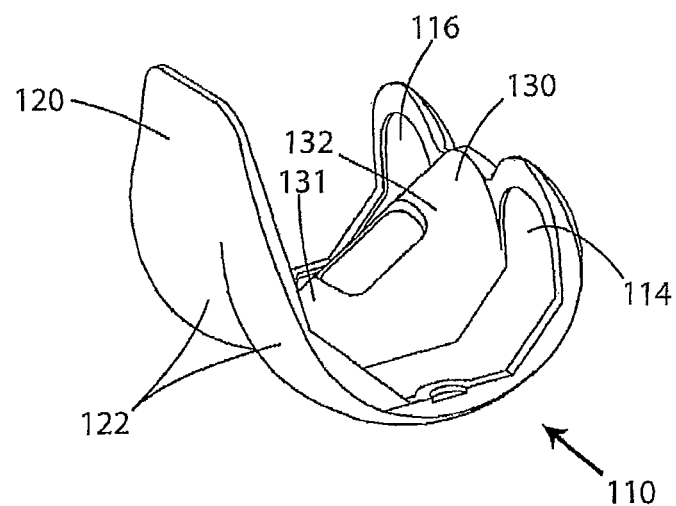
FIG. 2 is a side perspective view of a femoral component according to one embodiment of the present invention that forms a part of a knee joint prosthesis.
Figure 3:
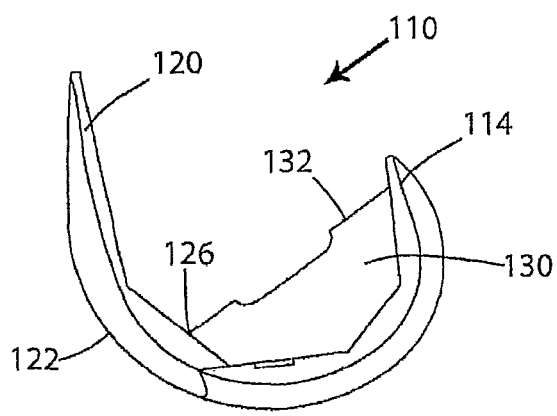
FIG. 3 is a side elevation view of the femoral component of FIG. 2.

The second means for reducing the amount of bone removal is the modification of the intercondylar box from a squared off configuration to more of a cylindrical shape as shown in FIG. 2, thereby removing less bone at the corners of the box. The intercondylar portion 130 is defined by an arcuate shaped wall 131 that likewise defines the roof 132 of the portion 130. The roof 132 can thus be thought of as the apex region of the arcuate shaped wall 131. The illustrated arcuate shaped wall 131 has a semi-circular shape or "rounded shape" that is designed to be received within a complementary rounded bone notch or opening that is shown in FIG. 11. The present intercondylar design thus does not include a well defined roof that is generally horizontal (parallel to a nominal base plane).

A comparison of the figures in FIG. 11 shows that significantly less bone is removed in the design of the present invention since the hard squared edges of the conventional femur box notch are absent in the rounded femur box notch made according to the present invention.

The cylindrical shape of the femur box notch made in the femur can be cut with a rotating cutter, such as a drill or reamer, which eliminates the additional stress concentrations created by the overcut slots that are created when cutting the box geometry of FIG. 11 with a sagittal saw. In other words, the cylindrical box geometry can be cut without creating stress concentrations in the corners where a sagittal saw would extend the cut past the edge of the box.

An opening 160 is preferably formed in the roof 132 of the intercondylar portion 130 and in particular, the opening 160 is formed in the arcuate shaped wall 131. Since the roof in the prior art intercondylar portion is a flat, planar surface, the opening was contained in the same plane; however, the arcuate shape of the wall 131 causes the opening 160 to lie not in a single plane, but instead, the opening 160 lies in an arcuate shaped surface. The opening 160 allows for placement of an intramedullary nail in the event of a distal femoral fracture after total knee replacement.

Figure 4:
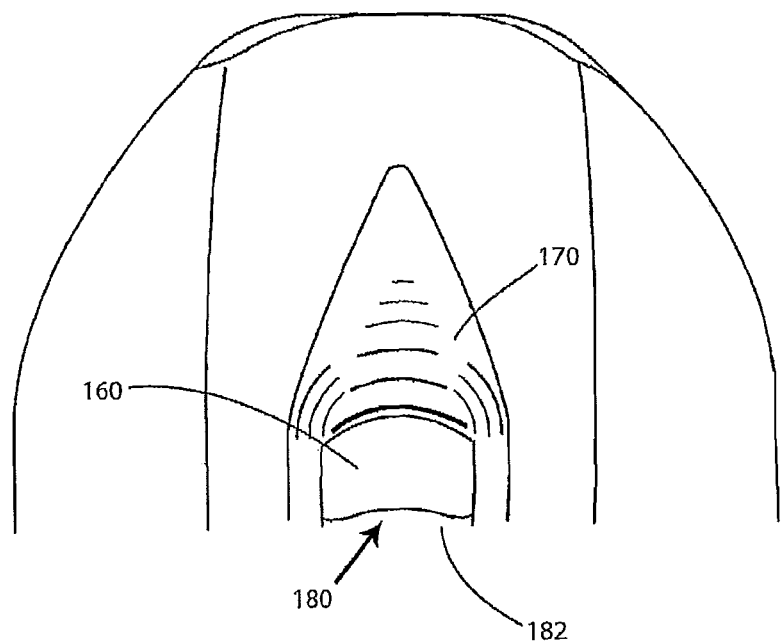
FIG. 4 is a bottom partial plan view of a cam surface of the femoral component of FIG. 2.
Figure 5:
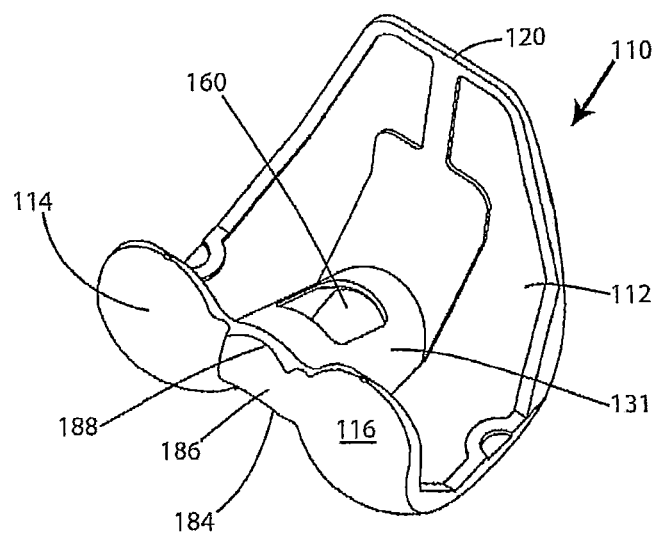
FIG. 5 is a top perspective view of the femoral component of FIG. 2.

As best shown in FIG. 4, an underside of the femoral component 110 includes an arcuate surface 170 (e.g., a curved saddle shaped surface). This arcuate surface 170 is located adjacent the opening 160 and faces the tibial component 200 (FIG. 8) when the two components 110, 200 are assembled. The arcuate surface 170 is proximate the patella portion 120. According to the present invention, this arcuate surface 170 is configured and dimensioned so as to mate with a complementary surface of the tibial component 200 when the components 110, 200 mate together as described below.

The femoral component 110 also includes a cam follower surface 180 that is located adjacent the opening 160 at the posterior side of the femoral component 110. In particular, the cam follower surface 180 is positioned between the condylar portions 114, 116. From the underside of the intercondylar portion 130, the cam follower surface 180 has a curved surface 182 that merges with a substantially concave portion 184 that then curves inward at 186 to merge with an upper curved surface 188.

The femoral component 110 can be made of a number of different materials, including a surgical grade, durable metal, such as a 316L stainless steel or a chrome-cobalt-molybdenum meeting ASTM Standard #F75. All surfaces which are external to the bone are preferably highly polished and the femoral component 110 can be symmetrical about a vertical antero-posterior center plane so that it can be used on either knee. It also can be asymmetrical (i.e., right or left knee specific).

The surfaces of the femoral component 110 that face the femur are generally flat and each of the condylar portions 114, 116, can be bounded by a small rib or flange, thus to provide a dam to increase cement pressurization and simplify clean up of excess cement. This pocketed feature also allows for beads or other biological attachment surfaces.

The tibial component 200 includes a tibial platform or tray 210 from which a tibial stem 212 extends downwardly and is constructed for insertion and attachment to the tibia. An upper surface 214 of the tibial tray 210 is constructed to receive and attach to a bearing component (tibial insert) 220 that is positionable between the femoral component 110 and the tibial tray 210. As described in greater detail below, the tibial insert 220 cooperates with the femoral component 110 to provide for the desired kinematics of the knee prosthesis.

The tibial insert 220 of the tibial component 200 is typically formed of a suitable plastic such as polyethylene, and more particularly, UHMWPE; however, other suitable materials can be used so long as they are intended for use in the current application. As shown best in FIGS. 7-9, the tibial insert 220 includes an oblong, rounded, disc-like plateau portion 222 having an upper surface that can be flat or have some other predetermined contour. A pair of laterally spaced-apart, oblong concavities 224, 226 is formed along the upper surface for receiving femoral condylar portions 114, 116 of the femoral component 110. The "nested" support of the femoral component 110 stabilizes the prosthetic joint, but still permits antero-posterior translation, lateral angulation and rotation, all of which are involved in normal function of the anatomical knee joint.

The tibial insert 220 also includes a base-like fixation portion 230 that extends from a bottom surface 228 of the plateau portion 222 to allow the tibial insert 220 to be attached to the tibial tray 210 using conventional techniques and methods.

The tibial insert 220 also includes a stabilizing post 240 that extends upward from the plateau portion 222 between the concavities 224, 226 and is positioned to be received in an intercondylar recess of the femoral component 110. The stabilizing post 240 is generally triangular in a lateral profile and is defined by flat, parallel side surfaces 242, an anterior face 250, and an opposite posterior face 260. The side surfaces 242 of the stabilizing post 240 are in sufficient clearance from the lateral walls of the femoral intercondylar recess to allow for normal lateral angulation and rotation when assembled with the femoral component 110 of the prosthetic knee joint. The posterior face 260 of the stabilizing post 240 includes a concave surface 262 at the inferior part of the posterior face 260 and furthermore, the posterior face 260 has a superior posterior surface 261 portion.

In contrast to conventional implants that have flat anterior faces, the anterior face 250 of the present invention does not have a flat design but instead, the anterior face 250 has been modified and constructed to create a lower stress contact condition when the patient hyperextends their knee. The anterior face 250 of the post 240 has a curved swept surface that takes the form of a saddle-like configuration where an at least substantially convex curve is swept along an at least substantially concave curve to form a saddle shape (i.e., this portion of the cam surface curves up in one or more directions and curves down in one or more directions).

A saddle shaped surface can be expressed in terms of saddle points. A saddle point for a smooth function, such as a curve or surface, is a point such that the curve/surface in the neighborhood of this point lies on different sides of the tangent at this point. The surface at a saddle point resembles a saddle that curves up in one or more directions, and curves down in one or more other directions (similar to a mountain pass). In terms of contour lines, a saddle point can be recognized, in general, by a contour that appears to intersect itself.

Figure 8:
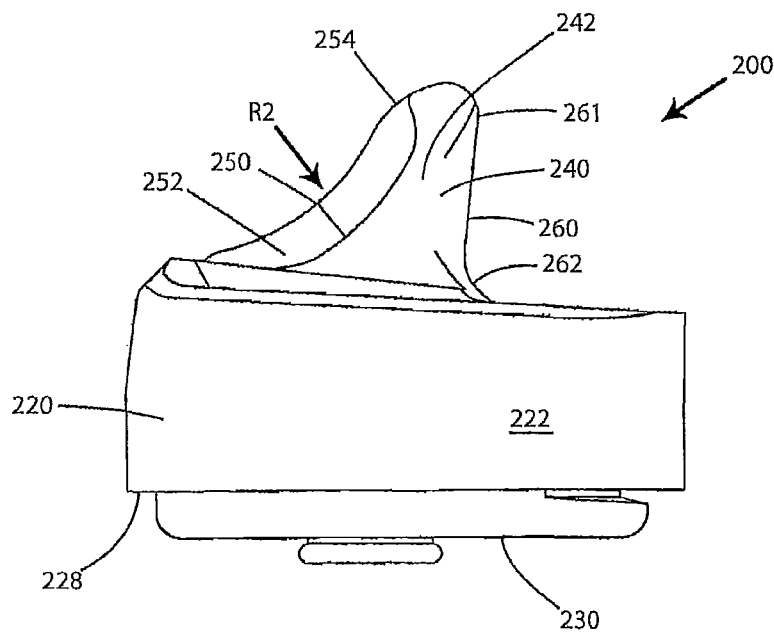
FIG. 8 is a side elevation view of the tibial insert of FIG. 7.

Thus, the anterior face 250 has a generally convex shape in a lateral or transverse direction, while in a longitudinal direction (from the inferior part to the superior part) the anterior face 250 transitions from a concave portion 252 at the inferior part of the anterior face 250 to a convex portion 254 at a superior part of the anterior face 250, as observed in a longitudinal direction and as shown in FIG. 8. In other words, the swept curved nature of the anterior face 250 is defined by a transition in the longitudinal direction from the concave portion 252 at the base of the post 240 to the convex portion 254 at the top of the post 240 (while at the same time, the anterior face 250 has a convex shape in a transverse direction (side-to-side direction perpendicular to the longitudinal direction) from the inferior part to the superior part so as to create the saddle configuration). It will be appreciated that the shape of the portion 254 at the top of the post is not critical since its illustrated convex shape simply provides a smooth way to connect the concave portion of the top of the post.

According to the present invention, the radius of curvature of the anterior face 250 is selected in view of a complementary radius associated with the femoral component 110. In particular, the radii are selected so that they are not identical, but instead, there is a slight mismatch in the radii where the radius on the tibial component 200 (i.e., the tibial post 240) is less than the femoral radius. In other words, the exact sizes of the radii are not critical so long as the radius of curvature of the anterior face 250 is a predetermined percentage of the femoral radius that results in a mismatch between the radii and the components 110, 200 to help assure that the contact between the components 110, 200 occurs at the center of the tibial post 240 instead of at lateral edges of the post 240. In one embodiment, the radius on the tibial component 240, and in particular on the anterior face 250, is approximately 95% of the femoral radius which is measured along the arcuate surface 170 (e.g., a curved saddle shaped surface that is complementary to the curved saddle shaped surface of the tibial post 240). FIG. 10 shows a transverse cross-section to illustrate the mating of the two saddle shaped surfaces, one associated with the femoral component 110 and the other with the tibial component 200.

It will be appreciated that the present invention is directed to improvements and modifications to the anterior cam (surface 170) on the femoral component 110 and the anterior cam (surface 250) on the tibial component 200. It will be appreciated that due to their saddle shaped constructions, both surfaces 170 and 250 are described as being cam surfaces that are configured to engage with one another similar to how a traditional cam and cam follower engage one another.

Figure 9:
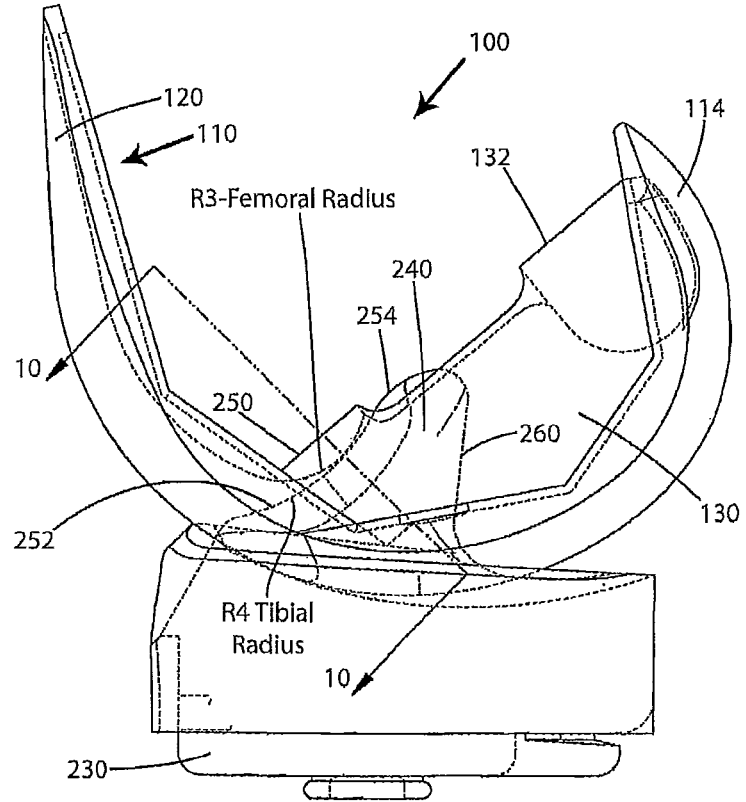
FIG. 9 is side elevation view of the femoral component of FIG. 2 mated with the tibial component of FIG. 7 in approximately 10 degrees of hyperextension.

As discussed above and in accordance with the present invention and as best shown in FIGS. 9 and 10, there is a relationship between the radius of curvature of the anterior face 250 and the radius of curvature of the complementary femoral component 110, and more particularly, the arcuate surface 170 formed on an underside thereof adjacent the opening 160. The radii of curvature of the surfaces/faces 170, 250 are not identical, but rather, there is a slight mismatch between the two in that the radius of curvature of the anterior face 250 is less than the radius of curvature of the surface 170. In one exemplary embodiment, the radius of curvature of the anterior face 250 is equal to or less than 95% of the femoral radius (i.e., the radius of curvature of arcuate anterior surface 170). For example, in one embodiment, the radius of the anterior face 250 of the post 240 is about 9.5 mm, while the radius of curvature of the complementary anterior face (surface) 170 of the femoral component 110 is about 10.0 mm (ratio of 95%). However, other radii are equally possible for the components 110, 200 and the radius on the tibial component 200 can be less than 95%, and even less than 90%, of the femoral radius.

Surface deformation in the anterior face of the post of the tibial component should not necessarily be expected; however, it can be caused by surgical malpositioning of the femoral and tibial components or by the designs of the components themselves or if a patient excessively hyperextends their knee. Retrievals of posterior stabilized total knee implants consistently show deformation patterns in this anterior face region. Implanting the femoral component in flexion or the tibial component tilted posteriorly may cause premature hyperextension contact. Conventional posterior stabilized implants, such as the one illustrated in FIG. 1) were not specifically designed to reduce the stresses on the anterior face, because patients were not expected to utilize the anterior surface of the post as a hyperextension stop.

This behavior between the components was modeled using finite element analysis (FEA). The stress state contributing to the pattern of deformation on the tibial post 240 was described and the effects of the above modifications that were made to the post-cam design for reducing the stresses on the anterior face 250 of the post 240 were examined.

Example

Computer models of the conventional implant of FIG. 1 (i.e., the Exactech Optetrak® PS total knee prosthesis) were modified to facilitate finite element meshing of the tibial post and the femoral anterior cam. The components were positioned in 10° of hyperextension. In this example, the anterior cam of the femoral component was modeled as a rigid indenter. The post of the tibial component was modeled as UHMWPE using a true stress-strain relationship. The constitutive model for this material was based on a von Mises yield surface with isotropic hardening. FE meshes were created, with the tibial post FE mesh being constructed using 8-noded hexagonal brick elements and the anterior cam surface being composed of 4-noded rectangular rigid elements. Because the post-cam mechanism is symmetric about the sagittal plane, a symmetric boundary condition was used and only half the mechanism modeled. The distal face of the post was fixed in all directions and the cam was allowed translation only in the direction of contact, i.e., perpendicular to the post at the contact point.

A load of 445N was used based on a 2D free body diagram of loads derived from gait data at maximum hyperextension. This load was applied to the rigid cam indenter, and its direction was perpendicular to the post at the point of contact. Analyses were carried out using three different sizes of the conventional implant of FIG. 1 and the modified design according to the present invention that is shown in FIGS. 2-10.

In all three sizes of the conventional implant, the maximum von Mises stress was located at the lateral edge of the anterior face of tibial post slightly inferior to the line-to-line contact point of the post and cam. The magnitudes were 34 MPa for size 2, 37 MPa for size 3 and 42 MPa for size 4 (all conventional designs). Maximum deformation of the UHMWPE post occurred at the same location as maximum stress and also increased with implant size; the values were 0.23 mm; 0.27 mm; and 0.36 mm for sizes 2, 3, and 4, respectively.

By modifying the design of the contact surfaces (e.g., anterior face 250 and surface 170), maximum von Mises stress decreased 35% to 24 MPa and maximum displacement decreased 37% to 0.17 mm compared to the size 3 conventional implant.

Stress contours in the FE models qualitatively matched the deformation pattern observed on retrieved implants. Maximum von Mises stress occurred on the lateral edge of the anterior tibial face, where contact was initiated. Stress was high in this region because the femoral cam indents the lateral edge before line-to-line contact occurs across the width of the face. Stresses increased with implant size because lateral edge indentation increased with size as the distance that the femoral cam must travel to reach line-to-line contact increased from size 2 to size 4. Contact in the new implant design of FIGS. 2-10 was initiated at the center of the post, eliminating lateral edge loading. The changes in the contact surfaces also broadened the contact area in the proximal-distal direction leading to a wider stress distribution.

In this manner, damage to the post 240 is reduced by modifying the shapes of the femoral and tibial components 110, 200 to reduce the contact stresses in the post. According to the present invention, the shape of the anterior surface 170 of the femoral component 110 and the anterior face 250 of the post 240 are modified to create a lower stress contact condition when the patient hyperextends their knee. The mismatch in the radii of curvatures between the two complementary mating surfaces 170, 250 assures that the contact between the components 110, 200 occurs at the center of the tibial post 240 instead of the lateral edges of the post 240.

The present design thus offers a more robust design with less contact surface stresses and less deformation of the anterior face of the stabilizing post that is part of the tibial insert.

As shown in FIG. 12, it will be appreciated that, in one embodiment, the anterior arcuate cam surfaces of each of the tibial post and the intercondylar portion of the femoral component can include a flat formed along the radius of curvature. In the case of the tibial post, the flat is formed along the convex anterior cam surface and in the case of the intercondylar portion, the flat is formed along the concave anterior cam surface. The width of the flat is relatively small and does not impact the above described mismatch in the radii of curvature of the two components. The flats should be positioned along their respective anterior cam surfaces so that they contact one another when the tibial and femoral components mate with one another. As illustrated, the flat is typically formed in a central area of each respective anterior cam surface. The anterior cam surface of the tibial component is thus at least substantially convex in that can include a small flat formed along its radius of curvature and the anterior cam surface of the femoral component is thus at least substantially concave in that it can include a small flat formed along its radius of curvature.

However, in other embodiment, as shown in FIGS. 2-11, the flats can be eliminated.

It will be appreciated by persons skilled in the art that the present invention is not limited to the embodiments described thus far with reference to the accompanying drawings; rather the present invention is limited only by the following claims.

What is claimed is:

1. A femoral component for a knee joint prosthesis comprising:
a body having an anterior side, a posterior side, a pair of laterally spaced condylar portions, and an intercondylar portion joining the condylar portions and including an intercondylar recess, wherein the intercondylar portion includes an arcuate shaped roof that is tangent to and extends between a pair of opposing side walls, wherein the arcuate shaped roof is defined by a single radius, the body having a cam surface located adjacent the intercondylar recess on the anterior side, the cam surface being defined by an at least substantially concave radius of curvature and a convex radius of curvature perpendicular to the concave radius of curvature so as to form a saddle shaped cam surface that is configured for articulation with a tibial insert.

2. A femoral component for a knee joint prosthesis comprising:
a body having an anterior side, a posterior side, a pair of laterally spaced condylar portions, and an intercondylar portion joining the condylar portions and including a recess, wherein the intercondylar portion has an arcuate shaped roof that is tangent to and extends between a pair of opposing side walls, wherein the arcuate shaped roof is defined by a single radius.

3. The femoral component of claim 2, wherein the arcuate shaped roof is configured to be inserted into an arcuate shape notch formed in the femur by removing bone.

4. The femoral component of claim 2, wherein an angle of the intercondylar portion is between about 20° to about 35°.

5. A femoral component for a knee joint prosthesis comprising:
a body having an anterior side, a posterior side, a pair of laterally spaced condylar portions, and an intercondylar portion joining the condylar portions and including a recess, wherein the intercondylar portion includes an arcuate shaped roof that extends between a pair of tangent side walls, wherein the arcuate shaped roof is defined by a single radius, the intercondylar portion being configured so as to permit reception into and mating with a femur box notch formed in a femur bone, the femur box notch being defined by a rounded top surface and a pair of parallel side walls so as to permit the arcuate shaped roof to seat against the rounded top surface and the side walls of the intercondylar portion of the femur box notch.

6. A femoral component for a knee joint prosthesis comprising:
a body having an anterior side, a posterior side, a pair of laterally spaced condylar portions, and an intercondylar portion joining the condylar portions and including a recess, wherein the intercondylar portion includes an arcuate shaped roof that is defined by a single radius and located between two side walls spaced apart from one another.

7. A femoral component for a knee joint prosthesis comprising:
a body having an anterior side, a posterior side, a pair of laterally spaced condylar portions, and an intercondylar portion joining the condylar portions and including a recess, wherein the intercondylar portion has an arcuate shaped roof, on an angle relative to a horizontal plane which is parallel to a base (ground) plane, that extends between a pair of tangent side walls on an angle, wherein the arcuate shaped roof is defined by a single radius.

8. The femoral component of claim 7, wherein the angle of the intercondylar portion is between about 20° to about 35°.

9. The femoral component of claim 1, wherein the arcuate shaped roof has a semi-circular shape.

10. The femoral component of claim 2, wherein the arcuate shaped roof has a semi-circular shape.

11. The femoral component of claim 5, wherein the arcuate shaped roof has a semi-circular shape.

12. The femoral component of claim 6, wherein the arcuate shaped roof has a semi-circular shape.

13. The femoral component of claim 7, wherein the arcuate shaped roof has a semi-circular shape.

* * * * *